US006438189B1

(12) United States Patent
Vourvopoulos

(10) Patent No.: US 6,438,189 B1
(45) Date of Patent: *Aug. 20, 2002

(54) PULSED NEUTRON ELEMENTAL ON-LINE MATERIAL ANALYZER

(75) Inventor: George Vourvopoulos, Bowling Green, KY (US)

(73) Assignee: Numat, Inc., Bowling Green, KY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/273,428

(22) Filed: Mar. 19, 1999

Related U.S. Application Data

(60) Provisional application No. 60/092,194, filed on Jul. 9, 1998.

(51) Int. Cl.[7] .................................................. G21G 1/06
(52) U.S. Cl. ........................................................ 376/159
(58) Field of Search ................................. 376/158, 159, 376/160, 157

(56) References Cited

U.S. PATENT DOCUMENTS

| | | | |
|---|---|---|---|
| 2,567,057 A | | 9/1951 | Crumrine |
| 3,082,323 A | * | 3/1963 | Chope et al. ............... 376/159 |
| 3,781,556 A | | 12/1973 | Taylor et al. |
| 4,361,534 A | * | 11/1982 | Borsaru et al. ............. 376/159 |
| 4,362,939 A | * | 12/1982 | Horiuchi et al. ......... 250/358.2 |
| 4,365,719 A | * | 12/1982 | Kelly ......................... 209/589 |
| 4,568,511 A | * | 2/1986 | Givens ........................ 376/159 |
| 4,582,992 A | * | 4/1986 | Atwell et al. ............. 250/359.1 |
| 4,702,379 A | | 10/1987 | Clayton et al. |
| 4,830,193 A | | 5/1989 | Clayton |
| 4,841,153 A | | 6/1989 | Wormald |
| 4,853,550 A | | 8/1989 | Schulz |
| 4,898,709 A | * | 2/1990 | Clayton ...................... 376/159 |
| 5,080,856 A | * | 1/1992 | Grenier et al. .............. 376/159 |
| 5,108,692 A | * | 4/1992 | Schoenig et al. ........... 376/159 |
| 5,109,227 A | | 4/1992 | Godfrey |
| 5,124,554 A | * | 6/1992 | Fowler et al. ........... 250/358.1 |
| 5,162,095 A | * | 11/1992 | Alegre et al. ................ 376/159 |
| 5,396,071 A | | 3/1995 | Atwell et al. |
| 5,412,217 A | * | 5/1995 | Miyashita et al. ..... 250/390.05 |
| 5,642,393 A | * | 6/1997 | Krug et al. .................... 378/57 |

FOREIGN PATENT DOCUMENTS

GB          2276237 A          9/1994

OTHER PUBLICATIONS

Knoll, G.F., Radiation Detection and Measurement, 2nd Ed., John Wiley & Sons, pp. 238–239, 1989.*
Anisimov et al., Increased Selectivity in Continuous Activation Analysis, Dec. 20, 1972, Radiochem.Radioanal.Letter , Vol. 12, pp. 283–288.*

* cited by examiner

*Primary Examiner*—Charles T. Jordan
*Assistant Examiner*—Daniel Matz
(74) *Attorney, Agent, or Firm*—John F. Salazar; Charles G. Lamb; Middleton Reutlinger

(57) ABSTRACT

An on-line material analyzer which utilizes pulsed neutron generation in order to determine the composition of material flowing through the apparatus. The on-line elemental material analyzer is based on a pulsed neutron generator. The elements in the material interact with the fast and thermal neutrons produced from the pulsed generator. Spectra of gamma-rays produced from fast neutrons interacting with elements of the material are analyzed and stored separately from spectra produced from thermal neutron reactions. Measurements of neutron activation takes place separately from the above reactions and at a distance from the neutron generator. A primary passageway allows the material to flow through at a constant rate of speed and operators to provide data corresponding to fast and thermal neutron reactions. A secondary passageway meters the material to allow for neutron activation analysis. The apparatus also has the capability to determine the density of the flowed material. Finally, the apparatus continually utilizes a neutron detector in order to normalize the yield of the gamma ray detectors and thereby automatically calibrates and adjusts the spectra data for fluctuations in neutron generation.

10 Claims, 6 Drawing Sheets

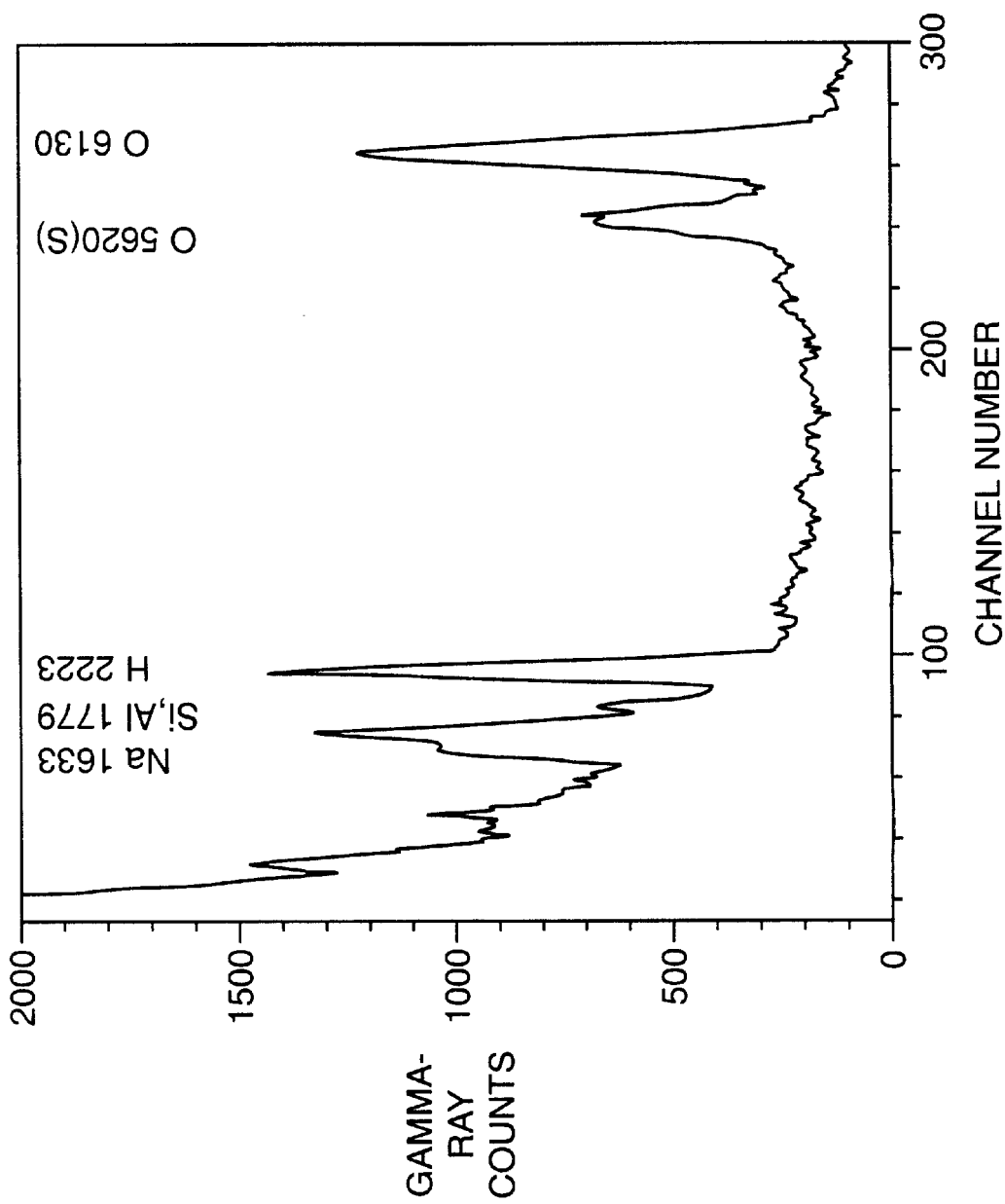

PULSED NEUTRON ELEMENTAL ON-LINE MATERIAL ANALYZER

This application claims priority to provisional application No. 60/092,194 filed Jul. 9, 1998.

BACKGROUND OF THE INVENTION

1. Field of the Invention

The present invention relates to a system which is used to determine the elemental content of materials such as coal and cement, by neutron irradiation. More particularly, the present invention is directed towards an apparatus which divides the flow of material into two paths, subjects the material to neutron bursts, and by utilizing the gamma rays emitted from the interrogated object, provides the ability to calculate the concentration of major and minor chemical elements in the material.

2. Discussion of the Prior Art

Neutron-based elemental on-line analyzers have been used by several industries such as the coal and cement industry over several decades. These analyzers provide a quantitative analysis of the major chemical elements contained in a material. Using neutron producing radioisotopic sources such as californium-252, these on-line analyzers determine the amount of H, N, C, Al, Si, Cl, Ca, S, Fe, etc. contained in the examined materials. Through these measurements, bulk properties such as density, volatile matter, calorific value etc. can be determined using algorithms such as:

Calorific value (BTU/lb)=a(%C)+b(%H)+c(%N)+d(%S)+e(%O)+ f(%ash)

However, there are limitations with the apparatus' used to determine these values.

With the currently available on-line elemental analyzers, the material moves on a conveyor belt or falls continuously through a chute. A neutron emitting radioisotopic source is placed on one side of the chute or conveyor belt, and a set of gamma-ray detectors is placed on the other side or at a position adjacent to the neutron source. The gamma-ray detectors analyze the gamma rays emitted from the coal sample after it is irradiated from the neutrons. These gamma rays act as fingerprints of the elements contained in the material. For example, a 4.43 MeV gamma ray is emitted from carbon, while a 5.42 MeV gamma ray is emitted from sulfur. The gamma-ray signals are transferred to the nuclear electronic modules where they are analyzed, and using the appropriate software, the elemental content of the material in the chute is determined.

The radioisotopic-source based systems, although they measure quite well most of the chemical elements, can be improved by replacing the low energy continuous neutrons emitted from the neutron source with higher energy pulsed neutrons emitted from a pulsed neutron generator. Some of the major advantages from such replacement are:

- Direct measurement of carbon (the main element in coal) without interference from other elements.
- Measurement of elements such as oxygen and sodium that cannot be measured with a californium-based system.
- Major reduction in the radiation hazard during removal and transportation of the source of neutrons.
- Reduction of the background in the gamma-ray spectrum.
- Ability to utilize a large number of nuclear reactions (fast neutron induced reactions, thermal neutron induced reactions, and neutron activation reactions) which allow improvement of the sensitivity and precision in the measurement of a specific chemical element.

Prior art devices which are disclosed in U.S. Pat. Nos. 5,396,071, 4,841,153, and 4,582,992 utilize isotopic neutron sources and do not allow separation of the measured spectra in spectra produced from fast neutron reactions, thermal neutron reactions, and neutron activation reactions thus limiting their accuracy and calculations of material content. Further prior art disclosed in U.S. Pat. No. 5,162,095 utilizes a neutron generator to examine the flow of bulk material. However, it only uses one pathway for the flow of the bulk material, acquiring at the same location with the same gamma-ray detector spectra from thermal neutron reactions and from neutron activation reactions. In this configuration, all materials (including metal structures, containers, belts, etc.) in the vicinity of the bulk material are also activated. This activation appears as background, obscuring the results from the activation of the bulk material. Furthermore, the prior art devices measure either a thermal neutron spectrum or a neutron activation spectrum, but not both simultaneously. Additionally, in this prior art configuration, approximately 50% of the time either spectrum is not measured.

SUMMARY OF THE INVENTION

The present invention is for an elemental on-line material analyzer which utilizes a pulsed neutron generator in combination with a specially designed material flow pathway in order to determine the composition of material flowing through the apparatus. The elements in the material interact with the fast and thermal neutrons produced from the pulsed generator while the material is resident in a first pathway. Spectra of gamma-rays produced from fast neutrons interacting with elements of the material are analyzed and stored separately from spectra produced from thermal neutron reactions. Measurements of neutron activation takes place separately from the above reactions and at a distance from the neutron generator in a second pathway designed particularly for activation reaction analysis.

The present invention is for an elemental on-line material analyzer based on a pulsed neutron generator which analyzes three spectra of data for composition determination. The apparatus utilizes a system which is composed of two pathways for the movement of the material to be analyzed. The main pathway is a chute or alternatively, a conveyor belt that is surrounded by a neutron generator and a system of gamma-ray and neutron detectors. The gamma-ray detectors in the main pathway are triggered by the neutron pulses and they accumulate gamma rays produced from fast neutron and thermal neutron reactions. The neutron detectors monitor the neutron production from the neutron generator and also measure the transmission of neutrons through the bulk of the material. The secondary pathway is a chute or conveyor belt used to measure the gamma rays from elements excited from neutron activation reactions. Elements such as sodium, silicon, aluminum and oxygen are some of the elements more accurately measured through neutron activation reactions. The material flows continuously through the main chute or conveyor, and the gamma ray detectors surrounding the main chute measure continuously the gamma-ray yield on the neutron pulse and off the neutron pulse. The material through the secondary chute flows in batches of a few kilograms each. Each batch is stopped next to the neutron generator where it is irradiated by the pulsed neutrons for a predetermined time. At the end of the irradiation period, the material is quickly moved to another location and a separate gamma-ray detector in the secondary pathway measures for a predetermined time the spectrum produced from the neutron activation. At the end of the measurement period, the material is weighed with an automatic electronic scale, and then is returned to the material flow exiting the main chute or conveyor. The analyzer also contains appropriate high voltage and low voltage power supplies for the production of neutrons, associated data collection electronics, and electrical devices that control the flow of the material samples through the main and the secondary chute. A computer-based data acquisition system receives the appropriate signals generated by the gamma-ray detectors and the various neutron detectors and converts them to digital values. These values are then analyzed by elemental characterization software which determines in real time the amount of the major and minor constituent elements present in the material under interrogation.

BRIEF DESCRIPTION OF THE DRAWINGS

A better understanding of the invention will be had upon reference to the following description in conjunction with the accompanying drawings in which like numerals refer to like parts and wherein:

FIG. 1b is a cutaway view indicating positions of the gates on the analyzer shown in FIG. 1a;

FIG. 2 is a time diagram generated by the pulsed neutron output of the apparatus of FIG. 1a;

FIG. 3 is a graph of the gamma-ray spectrum for fast neutron reactions generated by the apparatus of FIG. 1a;

DETAILED DESCRIPTION OF THE PREFERRED EMBODIMENT

Figure 1A:
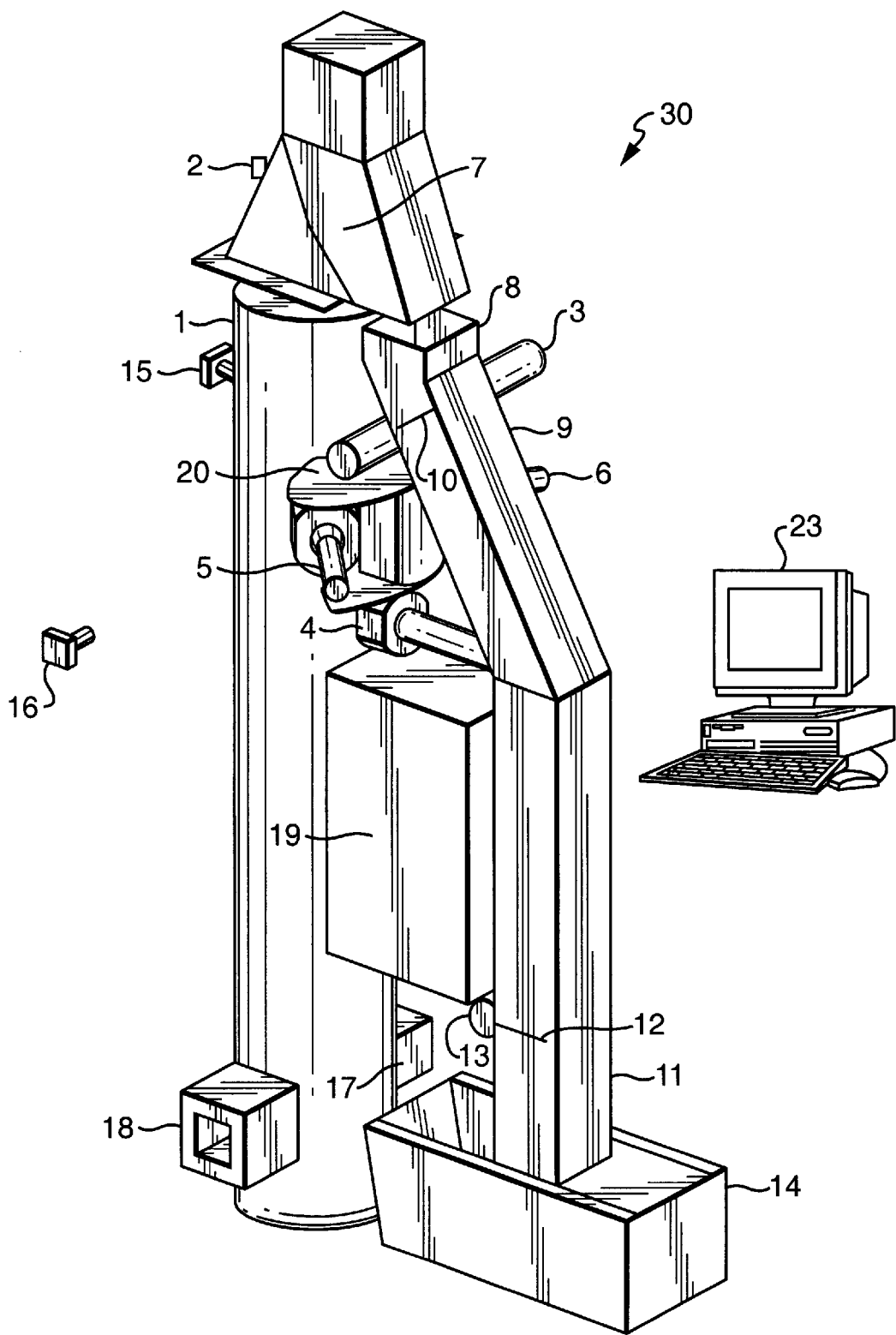
FIG. 1a is a schematic perspective view of the pulsed neutron-based material analyzer of the present invention.
Figure 1B:
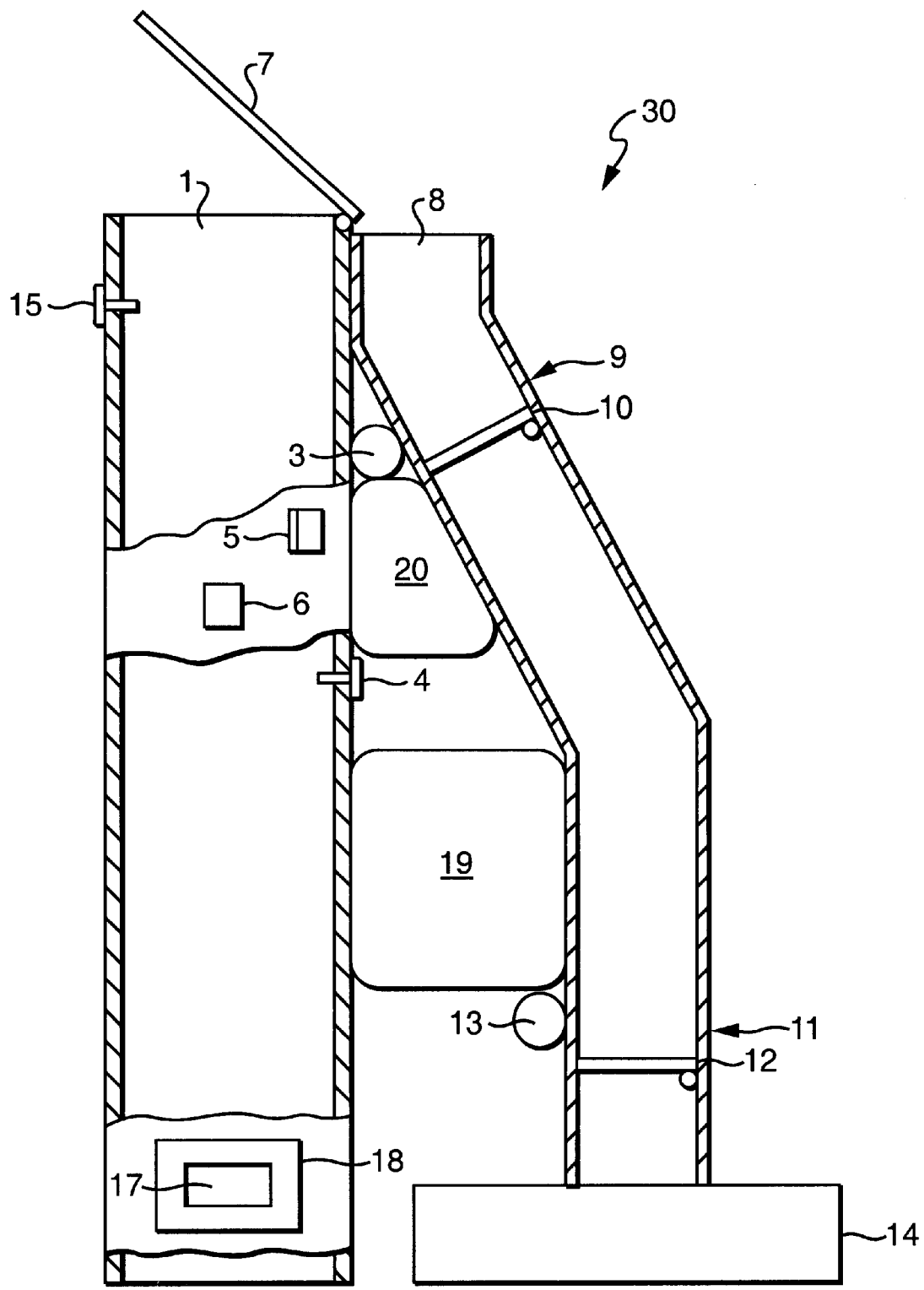
Figure 2:
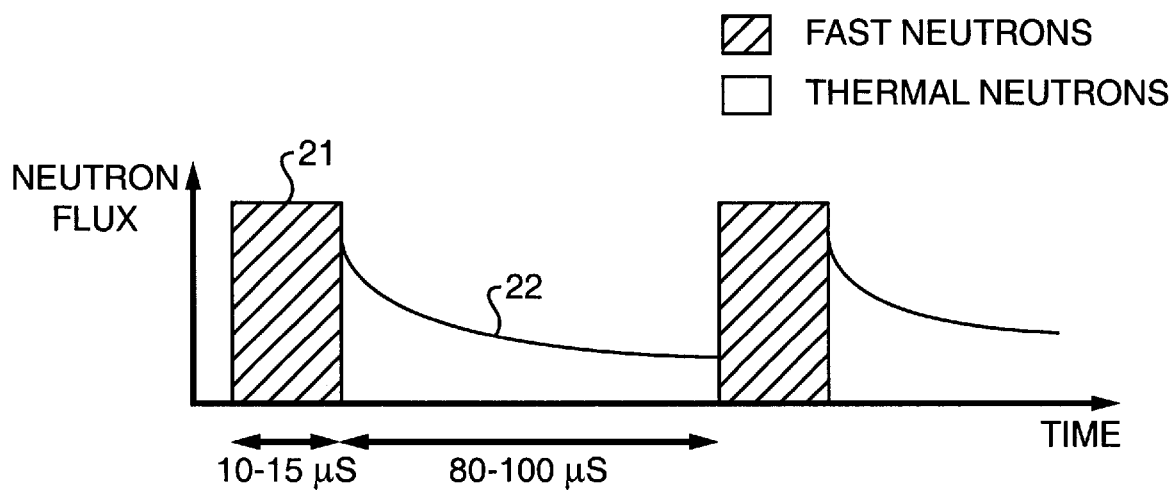

The apparatus 30 for a dual pathway pulsed neutron-based material analyzer 30 is shown schematically in FIG. 1a wherein each of the separate elements of the analyzer are clearly depicted. FIG. 1b shows a cutaway view of the pulsed neutron-based material analyzer 30 shown in FIG. 1a. The apparatus 30 is a chute-based elemental material analyzer. The material to be analyzed flows continuously through the main chute 1. The main chute 1 is maintained full of material at all times. A height control gauge 2 monitors the flow of the material through the main chute 1. Gauge 2 is an infrared transmitter-receiver. When gauge 2 detects absence of material, it sends a signal to the conveyor belt (not shown) that removes the material at the bottom of the chute 1 to slow down the material removal. This ensures that the main chute is always full of material to be analyzed and controls the speed of material through the chute. A neutron generator 3 emits pulses of fast neutrons that impinge on the material flowing through the main chute 1. The time sequence of the neutron pulses is shown in FIG. 2. Referring to FIG. 2, fast neutrons are emitted during the pulsed time period 21 which is around 10–15 µs followed by a measuring of gamma rays for about 80–100 µs which is required in order to properly generate the thermal neutron reactions. Both of these reactions generate measurements which are stored by the data acquisition system 23 for proper determination of material composition in chute 1.

The pulsed neutron generator 3 is computer 23 controlled. The analyzer contains a high voltage (larger than 100,000 Volts) power supply for the acceleration of deuterons, a 2,000–4,000 Volt supply for the pulsing of the deuteron beam and a low voltage supply for the deuteron ion source. The neutrons are generated by the impinging of the accelerated deuterons on a tritium target. The energy of the neutrons emitted from the generator must be larger than 6 MeV in order to properly cause the reactions necessary for elemental determination.

Electrical switching circuits are used to control gates 10 and 12 and thus the flow of material through main pathway 1 and secondary pathway 8. Each gamma-ray detector requires a high voltage (of the order of 1,000 volts) for the photomultiplier tube attached to it, and a low voltage supply (12 to 24 volts) for the preamplifier.

The apparatus 30 contains approximately thirty-five points which are monitored to determine its reliable operation. These points include the opening and closing of gates 10 and 12, the temperature stabilization of each gamma-ray detector, the high voltage for each gamma-ray and neutron detector, the adequate production of neutrons from the neutron generator and the radiation safety controls for the operators. These signals are fed to computer 23 and either alerts the operator of the analyzer or the computer 23 attempts to rectify the situation by altering a predetermined voltage.

Figure 3:
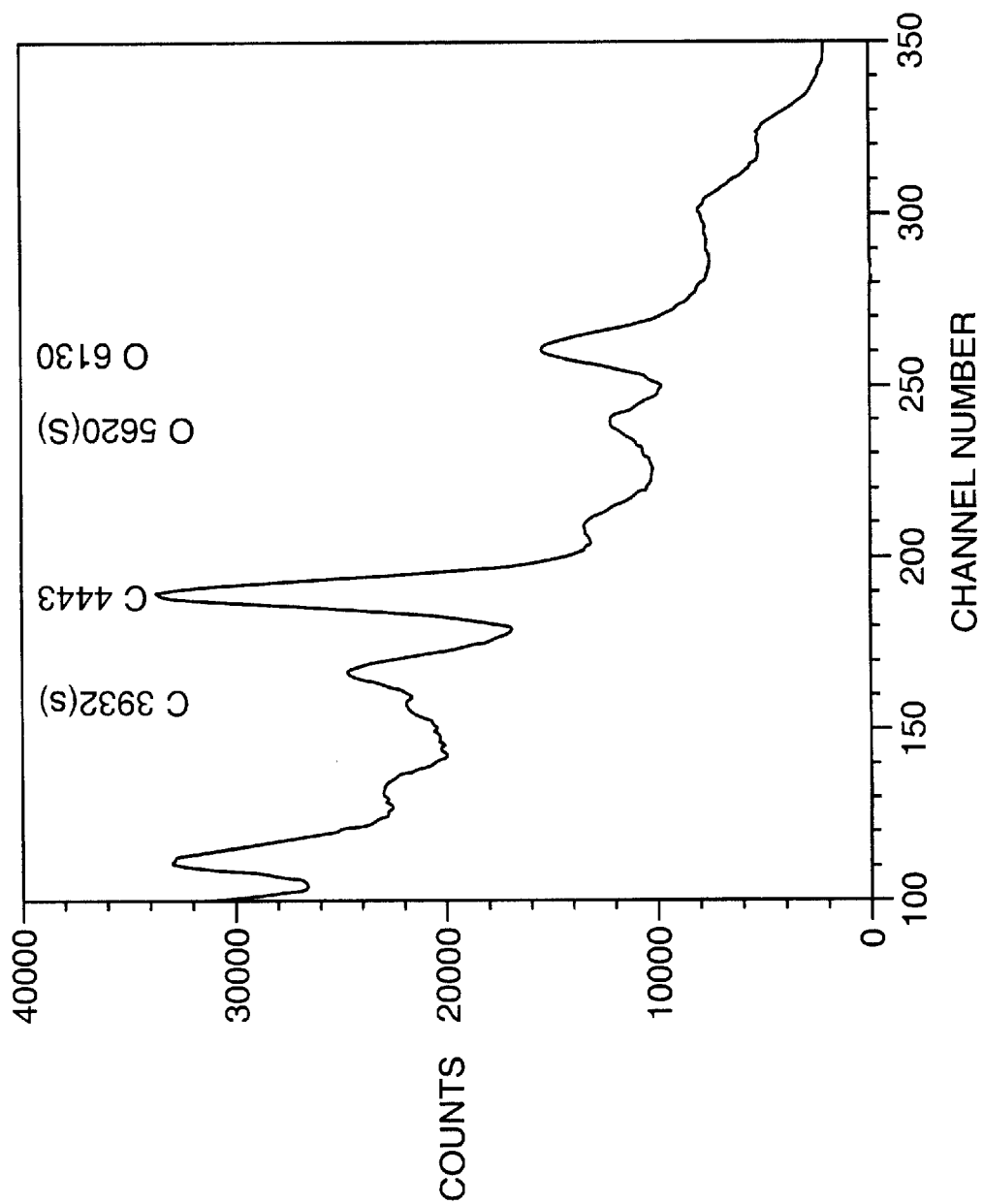

As represented in FIG. 2, each pulse 21 of neutrons is several microseconds wide and has a frequency of between 10 kHz and 14 kHz. These pulsed neutrons initiate the fast neutron reactions within the object being interrogated through main chute 1. Outgoing gamma rays from the material are detected by the gamma-ray detector 4 in chute 1 for a specified time period corresponding to the actual pulse time of the neutron pulse 21 from the neutron generator 3. The gamma rays representing fast neutron reactions are measured and recorded as a single spectrum of data during the time period 21 in the data acquisition system that resides in the computer 23. FIG. 3 shows a spectrum of gamma-rays produced from nuclear reactions induced from fast neutrons reactions. At the end of the neutron pulse 21, the fast neutrons are thermalized for a time period 22, shown in the FIG. 2 timing diagram.

Figure 4:
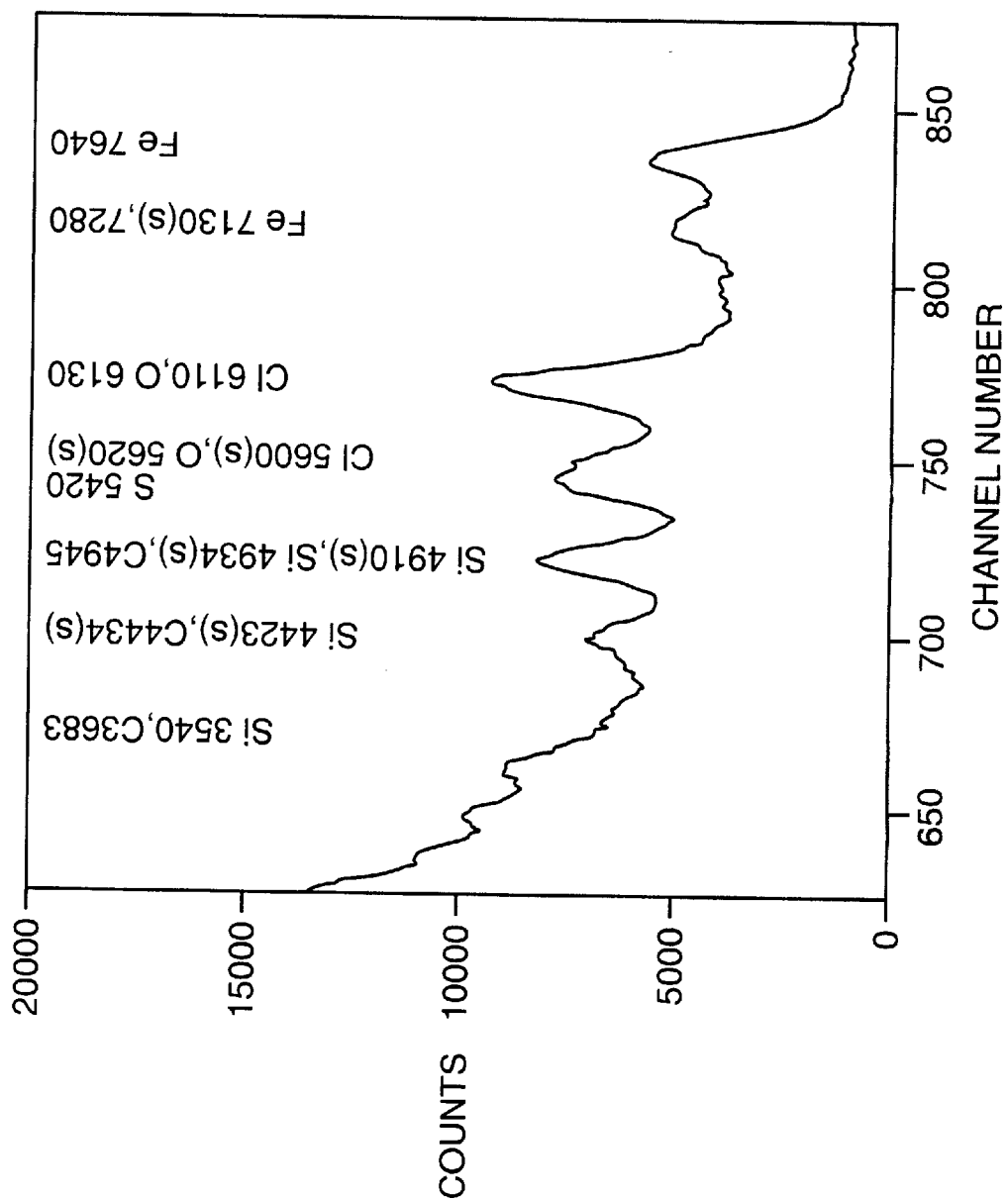
FIG. 4 is a graph of the gamma-ray spectrum for thermal neutron reactions generated by the apparatus of FIG. 1a; and, FIG. 5 is a graph of the gamma-ray spectrum for neutron activation reactions.

During the time thermalization period 22, the thermalized neutrons initiate capture reactions with the material in main chute 1 and those capture reactions are recorded and translated into an appropriate spectrum of data similar to that of FIG. 3. The gamma rays from the thermal neutron or capture reactions are detected by the detectors 5 and 6, and they are stored in a separate spectrum in computer 23. FIG. 4 shows a spectrum of gamma-rays produced from nuclear reactions induced from thermal neutrons.

Unfortunately, information from fast neutron reactions and thermal neutron or capture reactions only provide a partial framework for analysis of element composition. Neutron activation reactions must be detected and used in the modeling software in computer 23. Thus, spectra from all three can be used to accurately pinpoint the true composition of the material. However, these activation reactions take significantly longer to initiate as compared to thermal and fast reactions. A secondary chute 8 is thus provided to give a means for generating and detecting activation reactions in an environment separate and distinct from that generating thermal and fast reactions.

While the material flows through the main chute 1, a gate 7, shown in both FIGS. 1a and 1b diverts for a predetermined time period a predetermined amount of material (usually a few kilograms) to the secondary chute 8. This pre-determined time period is dependant upon the half life of the element of interest and varies between seconds to minutes. The amount of diverted material is controlled by the duration of time gate 7 remains open or raised. The diverted material is stopped at position 9 with a gate 10, and the material in the secondary chute 8 is irradiated from the pulsed neutron generator 3 for a pre-determined time period. This time period depends on the particular chemical element under investigation. For example, if the element sodium is to be measured, the sample will be irradiated at position 9 for approximately 30 seconds. At the end of the irradiation period, gate 10 opens and the sample falls under gravity to position 11 where another gate 12 stops it. At this position 11, a gamma-ray detector 13 measures for approximately the same duration as the irradiation time (e.g. for sodium it will measure for approximately 30 seconds) the gamma rays from the radioactivity built in the sample. The gamma rays detected from detector 13 are also stored in computer 23. FIG. 5 shows a spectrum of gamma-rays produced from nuclear reactions induced from neutron activation. At the end of the measuring period, gate 12 opens and the material falls onto a scale 14 where it is weighed. Following the weighing of the irradiated sample, the material in the secondary chute returns to a conveyor system which also has the material that flows through the main chute.

The gamma-ray spectra measured by the detectors 4, 5, 6, and 13, are composed of several gamma rays produced from chemical elements contained in the interrogated object. The spectra are stored in computer 23. The analysis of the spectra and the extraction of the gamma-ray yield for each element of interest is accomplished through a data de-convolution process which analyzes the response from the detectors and determines the chemical content and makeup of the object being interrogated. Through utilization of the apparatus of the present invention, this de-convolution process is made possible due to the ability of obtaining reactions from fast neutron reactions, thermal neutron reactions and neutron activation. This data more accurately determines the content of the material being analyzed.

Along with the gamma-ray detectors 4, 5, 6 and 13 which measure the gamma rays emitted from the irradiation of the material, there is also a gamma-ray detector 17 which measures the density of the material that flows through the chute. The number and size of the detectors 4, 5 and 6 as well as their location are dictated by the number of neutrons/pulse emitted by the neutron generator and also the maximum number of counts per second that a given detector can detect without being saturated and thereby becoming ineffective.

A cesium gamma-ray source 18 is shielded and collimated so that the emitted gamma-rays from the source are directed towards the material that lies between the source 18 and the detector 17. The gamma ray source 18 in combination with detector 17 is calibrated and the number of gamma rays from the source 18 that are seen by the detector 17 give an accurate measure of the density of the flowing material within main chute 1.

Detectors 15 and 16 are neutron detectors. Neutron detector 15 measures the fraction of the fast neutrons emitted from the neutron generator 3 that traverse the material in the main chute 1 without losing any energy, as well as the fraction of the fast neutrons that have lost nearly all of their energy (thermal neutrons) as they traverse the material in main chute 1. The measurement of the combination of fast and thermal neutrons is used for the establishment of the total hydrogen content of the material sample, and subsequently the moisture of the flowing material. Neutron detector 16 is a monitor of the fast neutron yield from the neutron generator. By measuring the number of fast neutrons emitted per unit time (e.g. per minute) the neutron generator yield is monitored, and any fluctuations or normal diminishing of the generator output are used to normalize the yield of the gamma ray detectors 4, 5, 6 and 13 and of the neutron detector 15.

To avoid any further irradiation of the material from neutrons emitted from the neutron generator 3 when the sample in the secondary chute 8 is measured at position 11, radiation shielding 19 is provided to separate gamma ray detector 13 from the generator 3.

Radiation shielding 19 is composed of neutron absorbing materials such as boric acid or borated polyethylene, and is placed between the neutron generator 3 and gamma-ray detector 13. Radiation shielding is also provided around the gamma-ray detectors 4, 5, and 6. Shielding 20 directly below neutron generator 3 adjacent to main chute 1 is composed of high atomic number material such as lead or tungsten, and shields the gamma-ray detectors 4, 5 and 6 from gamma rays generated by the neutron generator 3. To minimize the irradiation of the detectors themselves from neutrons, detectors 4, 5, and 6, have a concentric jacket composed of materials such as boron nitride or lithiated compounds that have a high thermal neutron absorption cross section.

The gamma-ray detectors 4, 5, 6, 13, and 17 are scintillator detectors such as sodium iodide or bismuth germinate. The neutron detectors 15 and 16 are helium-3 detectors, liquid scintillators, or a combination of lithium glass-liquid scintillator detectors.

With this emitter and detector arrangement, the pulsed neutron generator 3 irradiates simultaneously the material in the main chute 1, along with the material in the secondary chute 8. The material in the main chute 1 is flowing continuously, while the material in the secondary chute 8 is flowing in batches of preselected weight. The use of the pulsed neutron generator 3 instead of an isotopic source such as californium-252, allows the accumulation of gamma rays in three distinct spectra: one spectrum from fast neutron reactions, another spectrum from thermal neutron reactions, and a third one from neutron activation. The gamma-ray spectra from fast neutron reactions are accumulated only during the time the neutron pulse is on. The gamma-ray spectra from thermal neutron reactions are accumulated only during the time between the neutron pulses. The distinctly different spectra acquired from the three sets of nuclear reactions are shown in FIGS. 3, 4, and 5.

The arrangement shown in FIG. 1a and the discussion concerning the arrangement of the detectors can also be accommodated in a horizontal arrangement with the material moving on a conveyor belt or other similar horizontal material transport configuration. Modification into this horizontal arrangement is well within one of ordinary skill in the art.

The foregoing detailed description is given primarily for clearness of understanding and no unnecessary limitations are to be understood therefrom for modifications will become obvious to those skilled in the art upon reading this disclosure and may be made without departing from the spirit of the invention or the scope of the appended claims.

What is claimed is:

1. An elemental on-line analyzer comprising:
   a first material pathway through which material to be analyzed passes;
   a second material pathway through which material to be analyzed passes;
   a pivotable gate to divide a predetermined amount of material between said first material pathway and said second material pathway at predetermined times;
   a pulsed neutron generator between said first pathway and said second pathway;

a plurality of gamma ray detectors in radiation detecting communication with material passing through said first and said second material pathways;

a data acquisition system operably connected to said gamma ray detectors;

wherein said on-line analyzer detects fast neutron reactions and thermal neutron reactions in said first material pathway for a first predetermined time period and neutron activation reactions in said second material pathway for a second time period.

2. The on-line material analyzer of claim 1 wherein said second material pathway is further comprised of a first gate at a predetermined position adjacent said pulsed neutron generator and a second gate at a predetermined position adjacent at least one of said plurality of gamma ray detectors.

3. The on-line material analyzer of claim 2 wherein said plurality of gamma ray detectors is comprised of a first gamma ray detector in said first material pathway to measure fast neutron reactions, a second and third gamma ray detector in said first material pathway to measure thermal neutron reactions, and a fourth gamma ray detector in said second material pathway to measure neutron activation reactions.

4. The on-line material analyzer of claim 3 wherein said data acquisition system obtains three spectra of gamma rays, a first spectrum from fast neutron reactions, a second spectrum from thermal neutron reactions and a third spectrum from neutron activation reactions.

5. The on-line material analyzer of claim 4 wherein said first spectrum is accumulated when said pulsed neutron pulse is on, said second spectrum accumulated between neutron pulses, and said third spectrum during said second predetermined time period in said second chute.

6. An elemental on-line material analyzer comprising:

a first continuously flowing material pathway through which material to be analyzed passes;

a second batch processing material pathway through which material to be analyzed passes;

a pivotable gate to divide a predetermined amount of material between said first material pathway and said second batch processing material pathway at predetermined times;

a pulsed neutron generator between said first pathway and said second pathway;

a first plurality of gamma ray detectors in said first material pathway and a second plurality of gamma ray detectors in said second material pathway;

a data acquisition system operably connected to said gamma ray detectors;

wherein said on-line analyzer detects fast neutron reactions and thermal neutron reactions in said first continuously flowing material pathway and neutron activation reactions in said second batch processing material pathway.

7. The material analyzer of claim 6 wherein at least one of said first plurality of gamma ray detectors measures fast neutron reactions during a neutron pulse of said generator, at least one of said first plurality of gamma ray detectors measures said thermal neutron reactions between pulses of said generator, and wherein said second plurality of gamma ray detectors measure said activation reactions in said second batch processing material pathway.

8. An elemental material on-line analyzer, comprising:

a first continuously flowing material pathway through which material to be analyzed passes;

a second batch processing material pathway through which material to be analyzed passes;

a pivotable gate to divide a predetermined amount of material between said first material pathway and said second batch processing material pathway at predetermined times;

a pulsed neutron generator adjacent said first continuously flowing material pathway and said second batch processing material pathway;

a first stop gate within said second batch processing material pathway adjacent and downstream of said pulsed neutron generator;

a first plurality of gamma ray detectors in said first material pathway and a second set of at least one gamma ray detector in said second material pathway;

a second stop gate within said second batch processing material pathway adjacent and downstream of said second set of at least one gamma ray detector;

a data acquisition system operably connected to said gamma ray detectors;

wherein said on-line analyzer detects fast neutron reactions and thermal neutron reactions in said first continuously flowing material pathway and neutron activation reactions in said second batch processing material pathway.

9. The on-line analyzer of claim 8 wherein said fast neutron reactions are measured during a pulse of said pulsed neutron generator, said thermal neutron reactions are measured between pulses of said pulsed neutron generator, and wherein material in said second material pathway is irradiated at said first stop gate simultaneously with said measurements of said thermal neutron reactions and said fast neutron reactions.

10. An elemental material on-line analyzer, comprising:

a first continuously flowing material pathway through which material to be analyzed passes;

a second batch processing material pathway through which material to be analyzed passes;

a pivotable gate to divide a predetermined amount of material between said first material pathway and the second batch processing material pathway at predetermined times;

a pulsed neutron generator adjacent said first continuously flowing material pathway and said second batch processing material pathway;

a first stop gate within said second batch processing material pathway adjacent said pulsed neutron generator;

a first plurality of gamma ray detectors in said first material pathway and a second set of at least one gamma ray detector in said second material pathway;

a second stop gate within said second batch processing material pathway adjacent said second set of at least one gamma ray detector;

a data acquisition system operably connected to said gamma ray detectors;

said one-line analyzer detects fast neutron reactions and thermal neutron reactions in said first continuously flowing material pathway and neutron activation reactions in said second batch processing material pathway, said fast neutron reactions measured during a pulse of said pulsed neutron generator, said material in said second material pathway irradiated at said first stop gate simultaneously with said measurements of said material neutron reactions and said fast neutron reactions.

* * * * *